(12) United States Patent
Ito et al.

(10) Patent No.: US 10,973,707 B2
(45) Date of Patent: Apr. 13, 2021

(54) WATER ABSORPTION TREATMENT MATERIAL COMPRISING GRANULAR CORE AND COATING CONTAINING POLYMER PARTICLES THEREIN

(71) Applicant: DAIKI CO., LTD., Tokyo (JP)

(72) Inventors: Hiroshi Ito, Tokyo (JP); Junji Yoshinaga, Tokyo (JP)

(73) Assignee: DAIKI CO., LTD., Tokyo (JP)

(*) Notice: Subject to any disclaimer, the term of this patent is extended or adjusted under 35 U.S.C. 154(b) by 219 days.

(21) Appl. No.: 16/020,355

(22) Filed: Jun. 27, 2018

(65) Prior Publication Data
US 2018/0303684 A1  Oct. 25, 2018

Related U.S. Application Data

(63) Continuation of application No. PCT/JP2016/052901, filed on Feb. 1, 2016.

(51) Int. Cl.
*B32B 5/16* (2006.01)
*A61F 13/537* (2006.01)
(Continued)

(52) U.S. Cl.
CPC ...... *A61F 13/53752* (2013.01); *A01K 1/0155* (2013.01); *A61F 13/15252* (2013.01); *A61F 2013/1526* (2013.01); *A61F 2013/530007* (2013.01); *A61F 2013/530189* (2013.01); *A61F 2013/530613* (2013.01); *Y10T 428/2998* (2015.01)

(58) Field of Classification Search
CPC ............................................. Y10T 428/2998

USPC ........................................................ 428/407
See application file for complete search history.

(56) References Cited

U.S. PATENT DOCUMENTS 5,724,915 A    3/1998  Ochi et al.
2008/0045916 A1*  2/2008  Herfert .................. A61L 15/60
                                                    604/372
(Continued)

FOREIGN PATENT DOCUMENTS

JP    H07-31314 A    2/1995
JP    H08-154514 A   6/1996
(Continued)

OTHER PUBLICATIONS

May 10, 2016 International Search Report issued in International Patent Application No. PCT/JP2016/052901.
(Continued)

*Primary Examiner* — Hoa (Holly) Le
(74) *Attorney, Agent, or Firm* — Oliff PLC

(57) ABSTRACT

The present invention provides a water absorption treatment material that has a structure suitable for obtaining a high level of water disintegrability. A water absorption treatment material is a water absorption treatment material that absorbs a liquid, and includes a granular core portion and a coating layer portion. The granular core portion has a granular shape. The granular core portion contains a first water-absorbent polymer. The coating layer portion covers the granular core portion. The coating layer portion contains a second water-absorbent polymer. The second water-absorbent polymer has a mean particle size smaller than the mean particle size of the first water-absorbent polymer.

11 Claims, 1 Drawing Sheet

(51) Int. Cl.
*A01K 1/015* (2006.01)
*A61F 13/15* (2006.01)
*A61F 13/53* (2006.01)

(56) References Cited

U.S. PATENT DOCUMENTS

2014/0190420 A1 7/2014 Ito et al.
2016/0316713 A1* 11/2016 Mochizuki ........... B01J 20/3208

FOREIGN PATENT DOCUMENTS

| | | |
|---|---|---|
| JP | H10-262482 A | 10/1998 |
| JP | 2000-116264 A | 4/2000 |
| JP | 2002-218855 A | 8/2002 |
| JP | 2002-262691 A | 9/2002 |
| JP | 2006-42830 A | 2/2006 |
| JP | 2006-333773 A | 12/2006 |
| JP | 2010-124804 A | 6/2010 |
| JP | 2014-103961 A | 6/2014 |
| JP | 2015-97505 A | 5/2015 |
| WO | 2013/099311 A1 | 7/2013 |
| WO | 2015-098361 A1 | 7/2015 |

OTHER PUBLICATIONS

May 10, 2016 Written Opinion of the International Searching Authority issued in International Patent Application No. PCT/JP2016/052901.

May 29, 2019 Search Report issued in European Patent Application No. 16 88 9214.

Dec. 27, 2017 Office Action issued in Japanese Patent Application No. 2014-164868.

Jul. 20, 2018 Office Action issued in Japanese Patent Application No. 2014-164868.

* cited by examiner

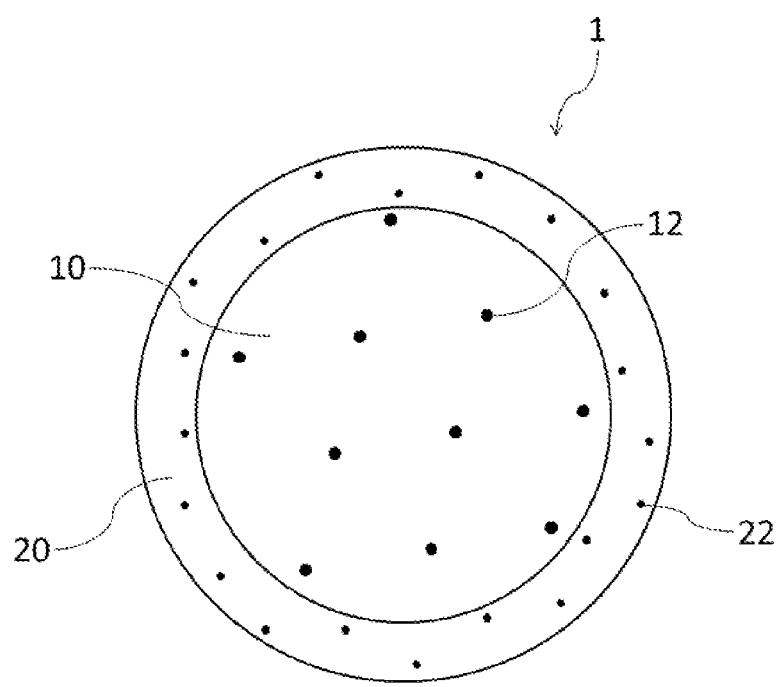

WATER ABSORPTION TREATMENT MATERIAL COMPRISING GRANULAR CORE AND COATING CONTAINING POLYMER PARTICLES THEREIN

CROSS REFERENCE TO RELATED APPLICATION

This is a Continuation of International Application No. PCT/JP2016/052901 filed Feb. 1, 2016. The contents of this application are hereby incorporated by reference in their entirety.

TECHNICAL FIELD

The present invention relates to a water absorption treatment material that absorbs human or animal excrement and other liquids.

BACKGROUND ART

Patent Document 1 discloses an excrement treatment material that is a kind of water absorption treatment material. This excrement treatment material includes a granular core portion and a coating layer portion that covers the granular core portion. The coating layer portion contains a water-absorbent polymer, and has a function of attaching grains of the excrement treatment material that have absorbed a liquid such as urine when in use to one another, and clumping them together.

CITATION LIST

Patent Document

Patent Document 1: JP 2006-333773A

SUMMARY OF INVENTION

Technical Problem

Water-absorbent polymers become sticky upon absorbing a liquid. For this reason, inclusion of a water-absorbent polymer in the coating layer portion improves the clumping ability of the water absorption treatment material after use. However, water-absorbent polymers also have the property of swelling upon absorbing a liquid. The water-absorbent polymer that has swollen in the coating layer portion blocks water from the outside from reaching the granular core portion. This lowers water disintegrability (the property of being able to disperse into water due to fibers or particles that are bound together quickly separating upon contact with water) of the water absorption treatment material when the water absorption treatment material after use is flushed down a flush toilet.

Solution to Problem

The present invention has been made in view of the problem described above, and it is an object of the present invention to provide a water absorption treatment material that has a structure suitable for obtaining a high level of water disintegrability.

A water absorption treatment material according to the present invention is a water absorption treatment material that absorbs a liquid, and includes a granular core portion that has a granular shape, and contains a first water-absorbent polymer; and a coating layer portion that is provided so as to cover the granular core portion, and contains a second water-absorbent polymer. The second water-absorbent polymer has a mean particle size smaller than a mean particle size of the first water-absorbent polymer.

In the water absorption treatment material, the mean particle size of the second water-absorbent polymer contained in the coating layer portion is smaller than the mean particle size of the first water-absorbent polymer contained in the granular core portion. Water-absorbent polymers, when finely pulverized, are less likely to swell upon absorbing a liquid. For this reason, by making the particle size of the second water-absorbent polymer smaller, it is possible to suppress swelling of the water-absorbent polymer in the coating layer portion. Accordingly, when the water absorption treatment material after use is flushed down a toilet, toilet flushing water easily passes through the coating layer portion and reaches the granular core portion. On the other hand, by making the particle size of the first water-absorbent polymer larger, collapse of the granular core portion caused by swelling of the water-absorbent polymer is promoted. As described above, with the water absorption treatment material of the present invention, toilet flushing water easily reaches the granular core portion, and the granular core portion can easily collapse. Accordingly, a high level of water disintegrability is obtained.

Advantageous Effects of Invention

According to the present invention, it is possible to implement a water absorption treatment material that has a structure suitable for obtaining a high level of water disintegrability.

BRIEF DESCRIPTION OF DRAWINGS

FIG. 1 is a schematic diagram showing a water absorption treatment material according to one embodiment of the present invention.

DESCRIPTION OF EMBODIMENTS

Hereinafter, an embodiment of the present invention will be described in detail with reference to the drawing. In the description of the drawing, the same elements are given the same reference numerals, and a redundant description will be omitted.

FIG. 1 is a schematic diagram showing a water absorption treatment material according to one embodiment of the present invention. A water absorption treatment material 1 is a water absorption treatment material that absorbs a liquid, and includes a granular core portion 10 and a coating layer portion 20. The water absorption treatment material 1 is used as, for example, an excrement treatment material for pet animals such as cats and dogs.

The granular core portion 10 has a granular shape. The granular core portion 10 has, for example, a spherical, elliptic, or cylindrical shape. The granular core portion 10 has a water absorbing property, and has a function of absorbing and retaining a liquid such as urine. As a material (core portion material) that constitutes the granular core portion 10, it is possible to use, for example, paper, used tea leaves, plastics, or bean curd lees. These materials are preferably used as the main material of the granular core portion 10. As used herein, the main material of the granular core portion 10 refers to one of the materials constituting the granular core portion 10 that accounts for the highest weight ratio in the granular core portion 10. The main material of the granular core portion 10 has a particle size of preferably 0.5 mm or less, and more preferably 0.3 mm or less.

The paper refers to a material composed mainly of pulp. Examples of the paper include ordinary paper, a vinyl chloride wallpaper classified product (paper obtained by classifying vinyl chloride wallpaper), a fluff pulp, a papermaking sludge (including a pulp sludge, the same applies hereinafter), and the like. The papermaking sludge is preferably a papermaking sludge that has been pulverized with a water content of 40 wt % or more. In the case where used tea leaves are used as the main material of the granular core portion 10, the used tea leaves are preferably pulverized with a water content of 45 wt % or more. As the plastics, it is possible to use, for example, a disposable diaper classified product (plastics obtained by classifying disposable diapers). The bean curd lees are preferably dried bean curd lees.

The granular core portion 10 contains a water-absorbent polymer 12 (first water-absorbent polymer). The mean particle size of the water-absorbent polymer 12 is preferably greater than 20 µm, and more preferably greater than 50 µm. As used herein, the mean particle size refers to the smallest aperture size through which 50 wt % or more of particles can pass when a water-absorbent polymer, which is an aggregate of a plurality of particles, are sieved. That is, "water-absorbent polymer having a mean particle size of greater than 20 µm" means that when the water-absorbent polymer is sieved using a sieve with an aperture size of 20 µm, only less than 50 wt % of the particles can pass through the sieve. The weight ratio of the water-absorbent polymer 12 in the granular core portion 10 is, for example, 5% or more and less than 30%.

The coating layer portion 20 covers the granular core portion 10. The coating layer portion 20 may cover the entire surface of the granular core portion 10, or may cover only a portion of the surface of the granular core portion 10. The coating layer portion 20 has a function (agglomeration function) of attaching grains of the water absorption treatment material 1 that have absorbed a liquid such as urine when in use to one another, and clumping them together. As a material (coating material) that constitutes the coating layer portion 20, it is possible to use, for example, paper, used tea leaves, plastics, or bean curd lees. These materials are preferably used as the main material of the coating layer portion 20. Also, it is preferable that the weight ratio of the coating layer portion 20 in the water absorption treatment material 1 is 5% or more and less than 10%. The granular core portion 10 may be visible through the coating layer portion 20 before the water absorption treatment material 1 absorbs a liquid.

The coating layer portion 20 contains a water-absorbent polymer 22 (second water-absorbent polymer). The mean particle size of the water-absorbent polymer 22 is smaller than the mean particle size of the water-absorbent polymer 12. It is preferable that the largest particle size of the water-absorbent polymer 22 (the particle size of a particle having the largest particle size of particles of the water-absorbent polymer 22 contained in the coating layer portion 20) is smaller than the smallest particle size of the water-absorbent polymer 12 (the particle size of a particle having the smallest particle size of the particles of the water-absorbent polymer 12 contained in the granular core portion 10). The mean particle size of the water-absorbent polymer 22 is preferably 20 µm or less, and more preferably 10 µm or less. As the water-absorbent polymer 22, it is possible to use a water-absorbent polymer that has been pulverized using a fine pulverizer such as a jet mill. The weight ratio of the water-absorbent polymer 22 in the coating layer portion 20 is, for example, 33% or more and less than 50%.

Advantageous effects of the water absorption treatment material 1 will be described. In the water absorption treatment material 1, the mean particle size of the water-absorbent polymer 22 contained in the coating layer portion 20 is smaller than the mean particle size of the water-absorbent polymer 12 contained in the granular core portion 10. Water-absorbent polymers, when finely pulverized, is less likely to swell even upon absorbing a liquid. For this reason, by making the particle size of the water-absorbent polymer 22 smaller, it is possible to suppress swelling of the water-absorbent polymer 22 in the coating layer portion 20. Accordingly, when the water absorption treatment material 1 after use is flushed down a toilet, toilet flushing water easily passes through the coating layer portion 20 and reaches the granular core portion 10.

On the other hand, by making the particle size of the water absorbent polymer 12 larger, collapse of the granular core portion 10 caused by swelling of the water-absorbent polymer 12 is promoted. As described above, with the water absorption treatment material 1, because the toilet flushing water easily reaches the granular core portion 10, and the granular core portion 10 can easily collapse, a high level of water disintegrability is obtained. Accordingly, it is possible to implement the water absorption treatment material 1 that has a structure suitable for obtaining a high level of water disintegrability.

Furthermore, finely pulverized water-absorbent polymers increase stickiness upon absorbing a liquid although swelling is suppressed. For this reason, making the particle size of the water-absorbent polymer 22 smaller is also advantageous in increasing the agglomeration function of the coating layer portion 20. Accordingly, the water absorption treatment material 1 has, not only excellent water disintegrability, but also excellent clumping ability.

As described above, making the particle size of the water-absorbent polymer 22 smaller is advantageous in improving the water disintegrability and the clumping ability of the water absorption treatment material 1. From this viewpoint, the mean particle size of the water-absorbent polymer 22 is preferably 20 µm or less, and more preferably 10 µm or less. On the other hand, in order to obtain a water-absorbent polymer 22 that has an excessively small particle size, a special apparatus or the like is required, which causes an increase in the manufacturing cost of the water absorption treatment material 1. From this viewpoint, the mean particle size of the water-absorbent polymer 22 is preferably 1 µm or more.

When the weight ratio of the water-absorbent polymer 22 in the coating layer portion 20 is 33% or more, a relatively large amount of water-absorbent polymer 22 is contained in the coating layer portion 20. Thus, the clumping ability of the water absorption treatment material 1 can be improved.

In this regard, in a conventional water absorption treatment material, if the amount of water-absorbent polymer in the coating layer portion is increased, the clumping ability is improved, but the water disintegrability decreases significantly. This is because an influence caused by the swollen water-absorbent polymer blocking water (toilet flushing water) from the outside is pronounced. Accordingly, in a conventional water absorption treatment material, improvement of the clumping ability and improvement of the water disintegrability inevitably have a trade-off relationship against each other. In contrast, in the present embodiment, swelling of the water-absorbent polymer 22 is suppressed by making the particle size smaller. Accordingly, even when the amount of water-absorbent polymer 22 is increased, water from the outside is unlikely to be blocked by the water-absorbent polymer 22. For this reason, it is possible to eliminate the above-described trade-off relationship, and improve the clumping ability while suppressing lowering in the water disintegrability.

In the case where a water-absorbent polymer 22 that has been pulverized using a fine pulverizer is used, it is possible to easily obtain a water-absorbent polymer 22 that has a mean particle size of 20 μm or less, and a small particle size variation.

As described above, making the particle size of the water-absorbent polymer 12 larger is also advantageous in improving the water disintegrability of the water absorption treatment material 1. From this viewpoint, the mean particle size of the water-absorbent polymer 12 is preferably greater than 20 μm, and more preferably greater than 50 μm.

In the case where the main material of the granular core portion 10 is paper, used tea leaves, plastics, or bean curd lees, a favorable water absorbing property can be imparted to the granular core portion 10, and therefore to the water absorption treatment material 1. Particularly when the main material of the granular core portion 10 is bean curd lees, the water disintegrability of the water absorption treatment material 1 can be further improved because bean curd lees are a highly water-disintegrable material.

In the case where a papermaking sludge or used tea leaves pulverized into a predetermined particle size is used as the material of the granular core portion 10, because these materials inherently contain a large amount of water, the papermaking sludge or used tea leaves are dried prior to pulverization when used for a conventional water absorption treatment material. However, if these materials are excessively dried, their fibers contract, which causes a reduction in the water absorbing property of the water absorption treatment material.

In this regard, in the case where a papermaking sludge that has been pulverized with a water content of 40 wt % or more, or used tea leaves that have been pulverized with a water content of 45 wt % or more is used, it is unnecessary to dry the papermaking sludge or the used tea leaves prior to pulverization. Accordingly, it is possible to avoid the reduction in the water absorbing property caused by excessive drying. In addition, because the papermaking sludge or the used tea leaves are not dried more than necessary before granulation, it is possible to increase porosity within a granule (granular core portion 10). As used herein, the porosity refers to the volume fraction of pores in a granule. Having a large porosity is advantageous in increasing the water absorbing property of the water absorption treatment material 1, as well as in increasing the water disintegrability of the water absorption treatment material 1.

Also, in order to increase the water disintegrability of the water absorption treatment material 1, it is advantageous that the main material of the granular core portion 10 is finely pulverized. This is because when the water absorption treatment material 1 after use is flushed down a toilet, the granular core portion 10 can easily collapse. From this viewpoint, the main material of the granular core portion 10 has a particle size of preferably 0.5 mm or less, and more preferably 0.3 mm or less.

Furthermore, in order to increase the water disintegrability of the water absorption treatment material 1, it is advantageous that the coating layer portion 20 has a small thickness. This is because water from the outside can easily pass through the coating layer portion 20 and reach the granular core portion 10. From this viewpoint, the weight ratio of the coating layer portion 20 in the water absorption treatment material 1 is preferably less than 10%. If, on the other hand, the thickness of the coating layer portion 20 is too small, the coating layer portion 20 cannot sufficiently exhibit the agglomeration function. From this viewpoint, the weight ratio of the coating layer portion 20 in the water absorption treatment material 1 is preferably 5% or more.

Next, an example of a method for manufacturing the water absorption treatment material 1 will be described. The manufacturing method includes a granulation step, a coating step, a sizing step, and a drying step.

In the granulation step, a core portion material containing the water-absorbent polymer 12 is pulverized to a predetermined size by using a pulverizer, and the pulverized core portion material is placed in a mixer at a predetermined rate, and mixed. Then, water is added as needed, and thereafter the core portion material is subjected to extrusion granulation using a granulator. In this way, a granular core portion 10 is obtained.

In the coating step, by using a coating apparatus or the like, a coating material containing the water-absorbent polymer 22 is attached to the periphery of the granular core portion 10. The attachment of the coating material may be performed by, for example, sprinkling or spraying the coating material. A coating layer portion 20 is thereby obtained.

In the sizing step, the water absorption treatment material manufactured in the previous step is passed through a sieve with a predetermined mesh size. Through this, only grains of the water absorption treatment material that satisfy a predetermined standard are extracted.

In the drying step, the water absorption treatment material extracted in the previous step is dried using a dryer. The water content of the granular core portion 10 is adjusted as appropriate through drying. It is thereby possible to prevent the water contained in the granular core portion 10 from moving to the coating layer portion 20 and reducing the water absorbing ability, and to prevent the occurrence of mold during storage of the water absorption treatment material 1.

LIST OF REFERENCE NUMERALS

1 Water Absorption Treatment Material
10 Granular core Portion
12 Water-Absorbent Polymer (First Water-Absorbent Polymer)
20 Coating Layer Portion
22 Water-Absorbent Polymer (Second Water-Absorbent Polymer)

The invention claimed is:

1. A water absorption treatment material that absorbs a liquid, the water absorption treatment material comprising:
   a granular core portion that has a granular shape, and contains a first water-absorbent polymer; and
   a coating layer portion that is provided so as to cover the granular core portion, and contains a second water-absorbent polymer,
   wherein:
   the first water-absorbent polymer has a mean particle size of greater than 20 μm and not greater than 50 μm, and
   the second water-absorbent polymer has a mean particle size smaller than the mean particle size of the first water-absorbent polymer.

2. The water absorption treatment material according to claim 1, wherein the second water-absorbent polymer has a mean particle size of 20 μm or less.

3. The water absorption treatment material according to claim 2, wherein the second water-absorbent polymer has a mean particle size of 10 µm or less.

4. The water absorption treatment material according to claim 1, wherein the second water-absorbent polymer is a water-absorbent polymer that has been pulverized using a fine pulverizer.

5. The water absorption treatment material according to claim 1, wherein a main material of the granular core portion is paper, used tea leaves, or plastics.

6. The water absorption treatment material according to claim 5, wherein the main material of the granular core portion has a particle size of 0.3 mm or less.

7. The water absorption treatment material according to claim 5, wherein the main material of the granular core portion is the paper, and the paper is a papermaking sludge that has been pulverized with a water content of 40 wt % or more.

8. The water absorption treatment material according to claim 5, wherein the main material of the granular core portion is the used tea leaves, and the used tea leaves are used tea leaves that have been pulverized with a water content of 45 wt % or more.

9. The water absorption treatment material according to claim 1, wherein a main material of the granular core portion is bean curd lees.

10. The water absorption treatment material according to claim 1, wherein a weight ratio of the coating layer portion in the water absorption treatment material is 5% or more and less than 10%.

11. The water absorption treatment material according to claim 1, wherein the granular core portion is visible through the coating layer portion before the water absorption treatment material absorbs the liquid.

\* \* \* \* \*